United States Patent [19]
deGuzman et al.

[11] Patent Number: 5,286,727
[45] Date of Patent: Feb. 15, 1994

[54] N-METHYLEPIAMAUROMINE, EPIAMAUROMINE AND CYCLOECHINULIN ANTIINSECTAN METABOLITES

[75] Inventors: Florecita S. deGuzman, Coralville, Iowa; Patrick F. Dowd, Peoria, Ill.; James B. Gloer, Iowa City, Iowa; Donald T. Wicklow, Peoria, Ill.

[73] Assignees: The United States of America as represented by the Secretary of Agriculture, Washington, D.C.; University of Iowa Research Foundation, Iowa City, Iowa; Biotechnology Research & Development Corporation, Peoria, Ill.

[21] Appl. No.: 843,567

[22] Filed: Apr. 27, 1992

Related U.S. Application Data

[62] Division of Ser. No. 732,776, Jul. 19, 1991.
[51] Int. Cl.⁵ .................. A61K 31/495; C07D 241/36
[52] U.S. Cl. ..................................... 514/250; 544/339; 544/341
[58] Field of Search ................ 544/339, 341; 514/250; A61K 31/495

[56] References Cited

U.S. PATENT DOCUMENTS 5,017,598  5/1991  Dowd et al. .................... 514/415

OTHER PUBLICATIONS

Gloer et al, J. Org. Chem. 53:5457 (1988).
Te Paske et al, J. Org. Chem. 55:5299 (1990).
Gloer et al, J. Org. Chem. 54:2530 (1989).
Takase et al. "Structure of Amauromine, A New Hypotensive Vasodilator Produced By Amaroascus Sp." Tetrahedron, vol. 41, 1985. pp. 3037-3048.
Takase et al. "Structure of Amauromine, A New Alkaloid with Vasolidating Activity Produced By Amauroascus Sp." Tetrahedron Lett., vol. 25, 1984. pp. 4673-4676.
Marchelli et al. "The Structures Of Five New Didehydropeptides Related To Neoechinulin Isolated From Aspergillus amstelodami" J. C. S. Perkin I, 1977. pp. 713-717.

Chang et al. "Chemical Abstracts" vol. 72, 1970, Abstract 67267X

Primary Examiner—Cecilia Tsang
Attorney, Agent, or Firm—Arnold, White & Durkee

ABSTRACT

Diketopiperazine compounds designated N-methylepiamauromine, epiamauromine and cycloechinulin have been isolated from the sclerotia of the fungi *Aspergillus ochraceus*. The compounds are effective for controlling Coleopteran and Lepidopteran insects. The compounds have the structures:

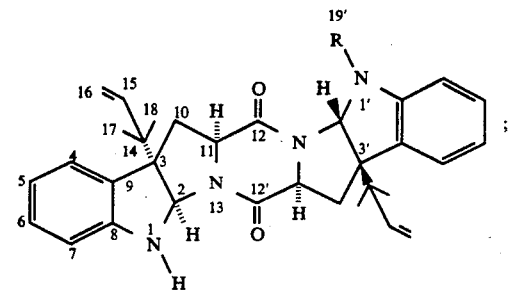

wherein: R is a hydrogen atom or a methyl group, such that the compound formed when R is a hydrogen atom is designated epiamauromine and the compound formed when R is a methyl group is designated N-methylepiamauromine; and cycloechinulin has the structure:

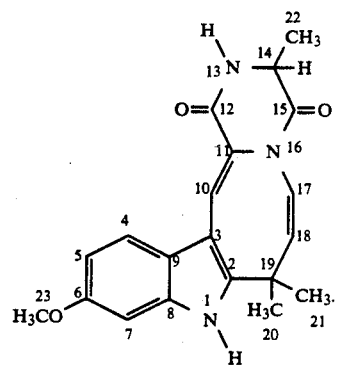

7 Claims, No Drawings

N-METHYLEPIAMAUROMINE, EPIAMAUROMINE AND CYCLOECHINULIN ANTIINSECTAN METABOLITES

This is a divisional of copending application Ser. No. 07/732,776 filed on Jul. 19, 1991.

BACKGROUND OF THE INVENTION

1. Field of the Invention

The present invention is generally related to diketopiperazine compounds. More specifically, the diketopiperazine compounds are used as insecticides for control of Lepidoptera and Coleoptera species.

2. Background of the Art

Certain fungi produce specialized resting bodies known as sclerotia as a means for surviving adverse environmental conditions which other fungal bodies cannot tolerate, such as harsh climate, nutrient deficiency and desiccation. Generally, sclerotia remain viable in soil for periods of several years, and provide primary inoculum for the producing species when conditions again become favorable for fungal growth. Sclerotia are formed under natural conditions or in solid substrate fermentations, but are not commonly produced in the liquid fermentation cultures generally employed in studies of microbial metabolites. Accordingly, many novel sclerotial metabolites of common fungi such as Aspergillus have not been characterized.

While sclerotia are known to contain biologically active secondary metabolites not found in other fungal parts or in liquid cultures, study of sclerotia as sources of novel metabolites has been limited. Investigation of large sclerotia (ergots) of *Claviceps purpurea* led to the discovery and medicinal use of ergot alkaloids.

Sclerotia have recently been recognized as a valuable potential source for natural antiinsectans. Many sclerotia, which are subjected to predation by fungivorous insects and anthropods during their period of dormancy in soil, have been shown to contain metabolites that exert adverse physiological effects on insects. Gloer et al. [*J. Org. Chem.* 53:5457 (1988)] and Wicklow et al. [*Trans. Br. Mycol. Soc.* 91:433 (1988)] disclose the isolation of four antiinsectan aflavanine derivatives from the sclerotia of *Aspergillus flavus* for use in controlling the dried-fruit beetle *Carpophilus hemipterus* (Nitidulidae:-Coleoptera). Te Paske et al. [*J. Org. Chem.* 55:5299 (1990)] disclose a related metabolite, aflavazole, which was isolated from extracts of *A. flavus* sclerotia. Gloer et al. [*J. Org. Chem.* 54:2530 (1989)] describe an insecticidal indole diterpene known as nominine found only in the sclerotia of *Aspergillus nomius* for the control of the corn earworm *Helicoperva zea* (Lepidoptera), formerly *Heliothis zea*. Nominine is also disclosed by Dowd et al. in U.S. Pat. No. 5,017,598 issued May 21, 1991, and entitled "Nominine, and Insecticidal Fungal Metabolite".

Marchelli et al. describe the compounds neoechinulins A-E which are didehydropeptides isolated from *Aspergillus amstelodami* [*J. C. S Perkin* I 713 (1977)]. Takase et al. disclose a hypotensive vasodilator produced from Amauroascus sp. known as amauromine [*Tetrahedron Lett.* 25:4673 (1984); *Tetrahedron* 41:3037(1985)].

There remains a continuing need for new insecticides because many agriculturally important insect species have developed a resistance to the most potent insecticides which are currently available. Moreover, environmentally tolerable replacements for these insecticides are declining. New natural, biodegradable insecticides which are relatively nontoxic to vertebrates and may be produced by fermentation processes are a cost effective replacement for known insecticides.

SUMMARY OF THE INVENTION

In order to satisfy the need for a cost effective, natural, biodegradable insecticide, one aspect of the present invention provides substantially pure diketopiperazine compounds. These compounds are isolated from the sclerotia of the fungus *Aspergillus ochraceus* and are effective for controlling Lepidopteran and Coleopteran insects. The compounds have the structures:

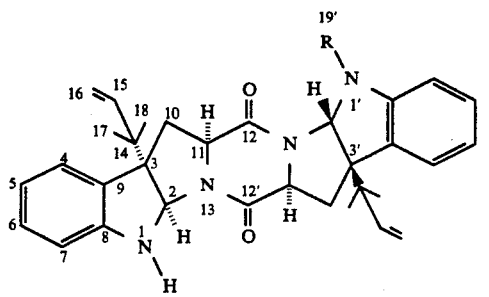

wherein: R is a hydrogen atom or a methyl group, such that the compound formed when R is a hydrogen atom is designated epiamauromine and the compound formed when R is a methyl group is designated N-methylepiamauromine; and cycloechinulin has the structure:

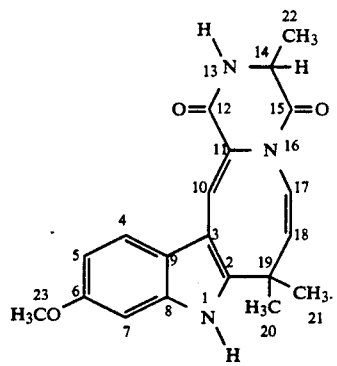

Another aspect of the present invention provides a composition for controlling insects containing an insecticide selected from the group consisting of N-methylepiamauromine, epiamauromine and cycloechinulin, and an inert carrier. The insecticidal compound is preferably present in the composition in an amount effecting insects of the Lepidopteran or Coleopteran species, such as *Helicoverpa zea* or *Carpophilus hemipterus*. An effective amount of the composition may be applied to a locus of insects in order to control the insects.

The present invention provides several substantially pure diketopiperazine compounds effective in controlling insects, insecticidal compositions containing a compound of the present invention and a method for controlling insects by applying the compositions to the locus of the insects.

The diketopiperazine compounds of the present invention have been designated N-methylepiamauromine, epiamauromine and cycloechinulin and are effective for controlling Lepidopteran and Coleopteran insects. The compounds have the structures:

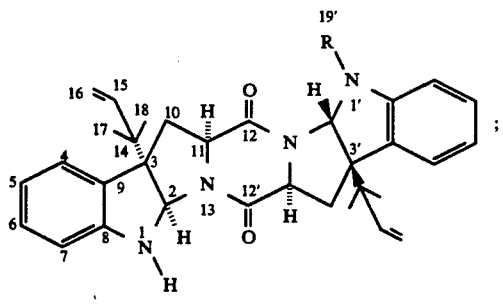

wherein: R is a hydrogen atom or a methyl group, such that the compound formed when R is a hydrogen atom is designated epiamauromine and the compound formed when R is a methyl group is designated N-methylepiamauromine; and cycloechinulin has the structure:

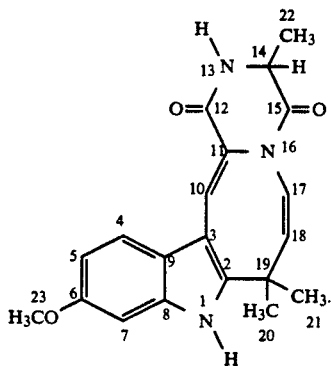

The compounds are isolated from the sclerotia of the fungus *Aspergillus Ochraceus*. A strain of the fungus *Aspergillus ochraceus* was deposited on Jun. 10, 1991 in the Agricultural Research Service Patent Culture Collection (NRRL) in Peoria, Ill. and has been assigned Deposit No. NRRL 18837. The culture deposit will be stored and made available to the public in accord with the provisions of the Budapest Treaty for the Deposit of Microorganisms. All restrictions on the availability of the culture deposit to the public will be irrevocably removed upon the granting of a patent disclosing the strain.

The sclerotia of *A. ochraceus* are produced by solid-substrate fermentation on corn kernels. They are ground by conventional means to a suitable particle size and are extracted with at least one solvent. Suitable solvents for the extraction could be readily determined by the skilled artisan and would include any solvents in which the radarin compounds of the present invention are soluble. Preferably, the ground sclerotia are extracted sequentially with hexane and chloroform.

Isolation and purification of each compound from the solvent extract is effected by the use of conventional techniques, such as high-performance liquid chromatography (HPLC), thin layer chromatography (TLC), silica gel column chromatography and countercurrent distribution (CCD). In the preferred embodiment of the invention, the hexane extract is subjected to reversed-phase HPLC to yield N-methylepiamauromine as a white solid. The chloroform extract is fractionated by HPLC affording fractions yielding epiamauromine as a white solid and cycloechinulin as a yellow solid. The details of the isolation procedure are described in Example 1, although the procedure is not limited thereto.

Commercial formulations including a compound of the present invention may be prepared directly from fungal extracts or from the fractions derived from the extracts. However, the formulations are prepared from a pure or a substantially pure radarin when a high degree of specificity is required. For example, if a high degree of predictability of the intended response by both target and nontarget species is required, a formulation prepared from a pure form of a radarin would be used. The formulation would then exclude other substances found in natural fungi which might have an adverse effect on activity or a toxic effect toward nontarget species.

Insecticidal compositions of the present invention include a compound as described above in combination with a suitable inert carrier as known in the art. Agronomically acceptable carries such as alcohols, ketones, esters and surfactants are illustrative. A compound of the present invention is present in the composition in an amount effecting the target species which is typically at least about 1.0 ppm. The concentration of the compound in an insecticidal composition will vary considerably depending upon the target species, substrate, method of application and desired response. Additional factors to be considered in determining an optimum concentration include phytotoxicity toward the treated plant and the tolerance of nontarget species.

The compounds of the present invention act to control pests by mechanisms including growth regulation, death inducement, sterilization, as well as interference with metamorphosis and other morphogenic functions. The resulting response is dependant on the pest species, insecticide concentration and method of application. The insecticidal compound is administered in an amount effecting one or more of the responses as may be predetermined by routine testing. Where the intended response is pest mortality, an "effective amount" is defined as the quantity of insecticidal compound which will effect a significant mortality rate of a test group as compared with an untreated group. The actual effective amount will vary with the species of pest, stage of larval development, nature of the substrate, the type of inert carrier, the period of treatment and other related factors.

The composition of the present invention are effective in controlling a variety of insects. Agronomically important insects such as those of the orders Lepidoptera and Coleoptera are of particular interest. However, the compounds and compositions of the present invention are not limited thereto.

The insecticidal compositions of the present invention are used to control insects by applying the composition to the locus of the pest to be controlled. When the radarin compound is intended as a stomach poison, it is applied in conjunction with an inert carrier to the pest diet. The composition is applied to plants by treating the leaf surfaces or by systematic incorporation. As a contact poison, any topical method of application will be effective, such as direct spraying on the pest or on a substrate which is likely to be contacted by the pest.

The following examples are presented to describe preferred embodiments and utilities of the present invention and are not meant to limit the present invention unless otherwise stated in the claims appended hereto.

EXAMPLE 1

Isolation and Purification of N-Methylepiamauromine, Epiamauromine and Cycloechinulin The culture of *Aspergillus ochraceus* Wilhelm (NRRL 18837) was obtained from the Agricultural Research Service (ARS) collection at the National Center for Agricultural Utilization Research in Peoria, Ill. Production of sclerotia was accomplished by solid substrate fermentation on autoclaved corn kernels and harvested as described by Quilico Res. Progr. Org. Biol. Medicin. Chem. 1:225 (1964). The intact sclerotia (21.6 g) were extracted at room temperature with hexane (200 ml, 1 day), then chloroform (100 ml, 3 days). After removal of the solvent in vacuo, the hexane extract (22 mg) was subjected to reversed-phase HPLC (9:1 MeOH:H$_2$O, 2 ml/min, 10 mm×25 cm column) to give 7 mg of N-methylepiamauromine.

The chloroform extract (0.1476 g), after removal of the solvent in vacuo, was fractionated through a column of Sephadex LH-20 (25–100μ) using 1:1 methylene chloride-hexane, then 1:1 methylene chloride-methanol as eluents. The fractions obtained with the 1:1 methylene chloride-hexane eluent were combined, concentrated, and then purified by HPLC as above to give 2.5 mg of epiamauromine and 4.1 mg of N-methylepiamauromine.

The fractions eluted with 1:1 methylene chloride-methanol were likewise combined, concentrated, and rechromatographed on Sephadex LH-20 using 2:1 chloroform-methanol, collecting 450 drops per fraction. Similar fractions were combined and the third combined fraction was purified by reversed phase HPLC to yield 1.1 mg of cycloechinulin.

In determining the properties of the compounds, heteronuclear multiple quantum correlation (HMQC) and heteronuclear multiple bond correlation (HMBC) data were obtained using a Bruker AMX600 spectrometer. All other $^1$H and $^{13}$C NMR spectra were obtained using a Bruker AC300 instrument. HREI and HRFAB mass spectra were recorded on a VG ZAB 250HF mass spectrometer, while low resolution EI mass spectra were recorded at 70 eV using a VG Trio 1 quadrupole mass spectrometer. Beckman Ultrasphere 5μ 10 mm×25 cm C$_{18}$-reversed phase column was used in all HPLC separations.

N-methylepiamauromine was isolated as a white solid; HPLC retention time 17.9 min; [α]—29.13 (c=4.6×10$^{-3}$, CHCl$_3$); UV (MeOH)λ$_{max}$213.5 (log ε4.4), 244.5 (log ε4.1),303.0 nm (log ε3.8); IR (film on NaCl plate) 3380, 1665, 1605 cm$^{-1}$; Electron impact mass spectrometry (EIMS) (70 eV) m/z (rel. int.) 522 (29), 453 (59), 384 (14), 255 (14), 184 (14), 171 (58), 157 (17), 144 (100); $^1$H NMR in Table 1; $^{13}$C NMR in Table 1; High resolution electron impact mass spectrometry (HREIMS), obsd., 522.3010; calcd. for C$_{33}$H$_{38}$O$_2$N$_4$, 522.2994.

Epiamauromine was isolated as a white solid; HPLC retention time 12.7 min under the conditions above; [α]—50.0 (c=1.8×10$^{-3}$, CHCl$_3$); EIMS m/z (rel. int.) 508 (0.03), 199 (61), 158 (20), 150 (7), 131 (100); $^1$H NMR in Table 1; $^{13}$C NMR in Table 1.

TABLE 1

NMR Data for N-methylepiamauromine and Epiamauromine

| | N-methylepiamauromine | | | Epiamauromine | | |
|---|---|---|---|---|---|---|
| Position | δ$_C$$^a$ | δ$_H$$^b$ (multiplicity, #H; J$_{HH}$) | Selective INEPT$^a$ (#C) | δ$_C$$^a$ | δ$_H$$^a$ (multiplicity, #H; J$_{HH}$) | HMBC$^c$ |
| 1 | — | 5.37(s, 1H) | 3, 8 | — | 5.36(br s, 1H) | 3, 8, 9 |
| 2 | 79.3 | 5.32(s, 1H) | 8, 9, 14 | 79.3 | 5.30(s, 1H) | 8, 9, 14 |
| 3 | 61.8 | — | — | 62.1 | — | — |
| 4 | 125.6 | 7.16(d, 1H; 7.5) | 3, 6, 8 | 125.7 | 7.16(dd, 1H; 7.8, 1.2) | 3, 6, 8 |
| 5 | 118.5 | 6.73(dt, 1H; 0.9, 7.5) | 7, 9 | 118.6 | 6.74(ddd, 1H; 1.2, 4.2, 7.2) | 7, 9 |
| 6 | 128.1 | 7.07(dd, 1H; <1, 7.2) | — | 128.3 | 7.08(dt, 1H; 1.2, 7.8) | 4, 8 |
| 7 | 108.7 | 6.56(d, 1H; 7.5) | 5, 9 | 108.8 | 6.56(ddd, 1H; 0.6, 1.2, 7.8) | 5, 9 |
| 8 | 148.3 | — | — | 148.4 | — | — |
| 9 | 131.4 | — | — | 131.4 | — | — |
| 10 | 36.0 | 2.45(dd, 1H; 9.3, 14.1) | — | 36.0 | 2.45(dd, 1H; 9.6, 13.8) | 9, 12 |
| | | 2.75(dd, 1H; 8.1, 12.5) | 2, 3, 9, 11, 12, 14 | | 2.75(dd, 1H; 9, 13.3) | 9 |
| 11 | 58.6 | 4.12(dt, 1H; 1.8, 9.3) | 10, 12 | 60.7 | 4.04(dt, 1H; 1.8, 9) | 10, 12 |
| 12 | 165.3 | — | — | 166.0 | — | — |
| 14 | 41.5 | — | — | 41.7 | — | — |
| 15 | 143.4 | 5.88(dd, 1H; 10.8, 17.2) | 14, 17 | 143.3 | 5.86(dd, 1H; 10.8, 17.4) | 14, 17, 18 |
| 16 | 114.6 | 5.07(dd, 1H; <1, 17.1) | — | 114.7 | 5.06(dd, 1H; 1.2, 17.4) | 14 |
| | | 5.10(dd, 1H; 0.9, 10.8) | — | | 5.09(dd, 1H; 0.6, 10.8) | 14 |
| 17 | 22.3 | 1.11(s, 3H) | 3, 14, 15 | 22.9 | 1.10(s, 3H) | 14, 15 |
| 18 | 22.3 | 0.95(s, 3H) | 3, 14, 15 | 22.5 | 0.93(s, 3H) | 14, 15 |
| 1' | — | — | — | — | 4.91(br s, 1H) | 3', 9' |
| 2' | 82.2 | 5.41(s, 1H) | 3', 8', 9', 14' | 77.6 | 5.30(s, 1H) | 8', 9', 14' |
| 3' | 60.7 | — | — | 61.8 | — | — |
| 4' | 128.9 | 7.06(dt, 1H; 0.9, 7.5) | — | 125.0 | 7.12(dd, 1H; 1.2, 7.2) | 3', 8', 9' |
| 5' | 117.2 | 6.65(dt, 1H; 0.9, 7.2) | 7', 9' | 118.9 | 6.72(ddd, 1H; 1.2, 4.2, 7.2) | 7', 9' |
| 6' | 124.6 | 7.10(dt, 1H; 0.9, 7.5) | — | 128.8 | 7.06(dt, 1H; 1.2, 7.8) | 4', 8' |
| 7' | 105.7 | 6.31(d, 1H; 7.8) | 9', 15' | 109.3 | 6.52(dm, 1H; 0.6, 1.2, 7.8) | 5', 9' |
| 8' | 151.2 | — | — | 150.0 | — | — |
| 9' | 129.3 | — | — | 129.0 | — | — |
| 10' | 37.0 | 2.48(dd, 1H; 6, 12.6) | — | 35.2 | 2.50(dd, 1H; 6, 12.6) | 9' |
| | | 2.25(dd, 1H; 11.1, 12.4) | 3', 12', 14' | | 2.35(dd, 1H; 10.8, 12.6) | 9', 13' |
| 11' | 60.6 | 3.96(ddd, 1H; 1.8, 6.2, 10.7) | 10', 12' | 62.0 | 3.90(ddd, 1H; 1.8, 6, 11.4) | 10', 13' |
| 12' | 168.3 | — | — | 168.0 | — | — |
| 14' | 40.7 | — | — | 40.8 | — | — |
| 15' | 143.4 | 5.80(dd, 1H; 10.8, 17.4) | 14' | 143.4 | 5.90(dd, 1H; 10.8, 17.4) | 14', 17', 18' |
| 16' | 114.3 | 4.98(dd, 1H; 0.9, 17.4) | — | 114.4 | 5.01(dd, 1H; 1.2, 17.4) | 14' |
| | | 5.03(dd, 1H; 0.9, 9.6) | — | | 5.07(dd 1H; 0.6, 10.8) | 14' |

TABLE 1-continued

| | NMR Data for N-methylepiamauromine and Epiamauromine | | | | | |
|---|---|---|---|---|---|---|
| | N-methylepiamauromine | | | Epiamauromine | | |
| Position | $\delta_C{}^a$ | $\delta_H{}^b$ (multiplicity, #H; $J_{HH}$) | Selective INEPT$^a$ (#C) | $\delta_C{}^a$ | $\delta_H{}^a$ (multiplicity, #H; $J_{HH}$) | HMBC$^c$ |
| 17' | 22.2 | 1.00(s, 3H) | 3', 15', 17' | 22.9 | 1.05(s, 3H) | 14', 15' |
| 18' | 22.9 | 0.89(s, 3H) | 3', 14', 15', 18' | 22.5 | 0.95(s, 3H) | 14', 15' |
| 19' | 33.0 | 2.98(s, 3H) | 2', 8' | | | |

$^a$75 MHz, in CDCl$_3$
$^b$300 MHz, in CDCl$_3$
$^c$600MHz, in CDCl$_3$

Cycloechinulin was isolated as a yellow solid: HPLC retention time 7.5 min; $[\alpha] - 23.3$ (c=6×10$^{-4}$, CHCl$_3$); UV (MeOH) $\lambda_{max}$214.5 (log $\epsilon$4.2), 267.0 (log $\epsilon$4.0), 300.5 (log $\epsilon$4.1), 377 nm (log $\epsilon$3.9); EIMS (70 eV) m/z (rel. int.) 351 (77), 336 (100), 308 (20), 296 (26), 293 (37), 280 (93), 265 (34), 252 (46), 25 (47), 237 (94), 225 (82), 222 (31), 197 (64); $^1$H NMR in Table 4; $^{13}$C NMR in Table 4; High resolution fast atom bombardment mass spectrometry (HRFABMS), obsd., 352.1671; calcd. for C$_{20}$H$_{21}$O$_3$N$_3$+H, 352.1661.

N-methylepiamauromine has the molecular formula C$_{33}$H$_{38}$O$_2$N$_4$ based on the HRMS data (m.z 522.3010, $\Delta$ −1.6 mmu). The presence of an amine NH group was deduced from the board IR absorption at 3380 cm$^{-1}$ and the exchangeable proton signal at 5.37 ppm in the $^1$H NMR spectrum. Two tertiary groups were inferred from the $^{13}$C NMR spectrum (165.3 and 168.3 ppm), the broad IR absorption at 1665 cm$^{-1}$, and the lack of further heteroatom-bonded protons.

Spin systems A-C and A'-C', as shown below in Scheme 1, were determined based on the results of $^1$H NMR decoupling and HETCOR experiments [Bax, J. Magn. Reson. 53:517 (1983); Bax and Morris, J. Magn. Reson. 42:501 (1981)].

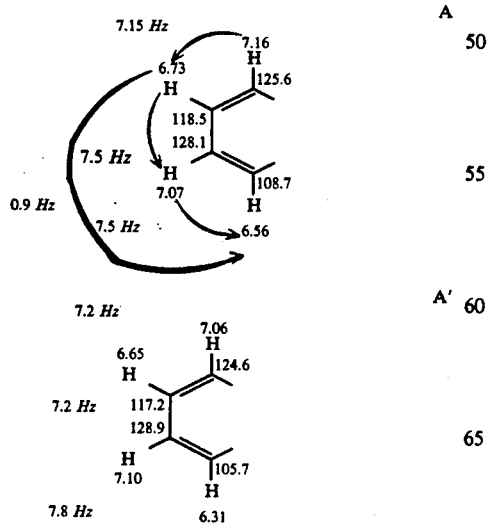

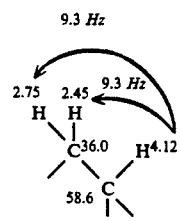

B

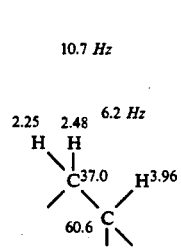

B'

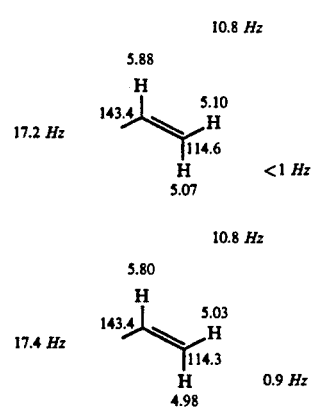

Results from selective insensitive nuclei enhanced by polarization transfer (INEPT) [Bax, J. Magn. Reson. 57:314 (1984)] experiments (Table 1) allowed the extension of partial structure A to the dihydroindole substructure D as shown below in Scheme 2.

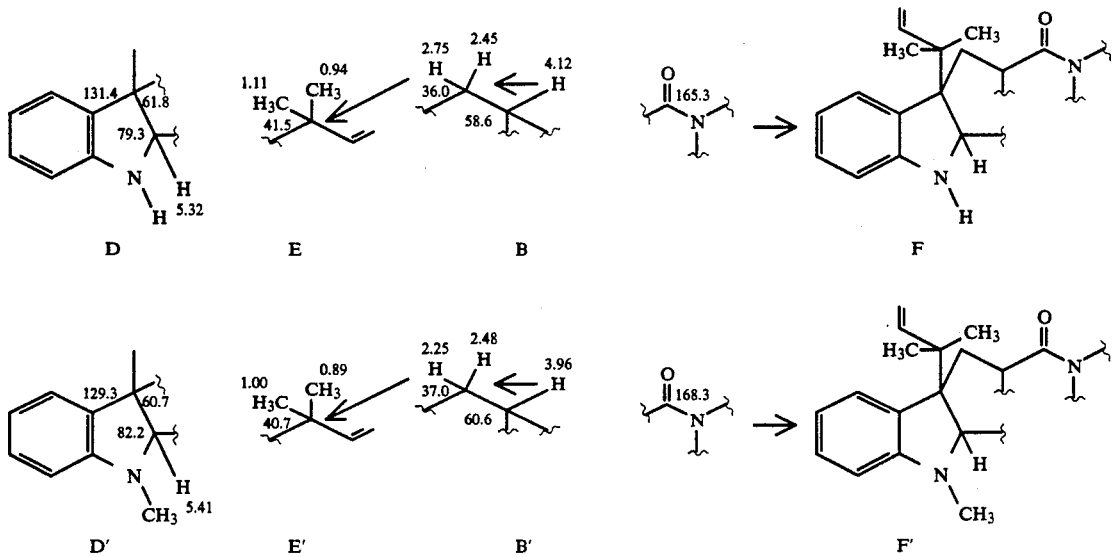

Selective irradiations of H-1, H-2, H-4, and H-6 all showed the C-8 signal, while irradiations of H-5 and H-7 showed the signal for C-9. H-1 and H-4 were also correlated with C-3. Similarly, partial structure A' was extended to the N-methyldihydroindole substructure D' based on an analogous series of selective INEPT correlations. The only difference in the second substructure was the presence of an N-methyl group. The N-methyl proton signal showed selective INEPT correlations to C-2 and C-8, while irradiation of H-2 showed the N-methyl carbon signal.

Spin systems C and C' were extended to 1,1-dimethyl-2-propenyl moieties E and E', respectively. Selective INEPT irradiations of the methyl proton singlets at 1.11 and 0.94 ppm, as well as the vinylic resonance at 5.88 ppm, all showed a signal corresponding to the quaternary carbon at 41.5 ppm, giving rise to the dimethylpropenyl unit E. Analogous results were obtained to give unit E'. Selective INEPT irradiation of both methyl proton signals of dimethylpropenyl group E also showed the carbon signal corresponding to C-3 of dihydroindole D, indicating that this dimethylpropenyl unit must be attached to the 3-position of D. Analogous correlations permitted linkage of dimethylpropenyl group E' and the N-methyldihydroindole D' (Scheme 2).

Spin system B can also be linked to dihydroindole D at the 3-position and to the amide carbon at 165.3 ppm, as shown by selective INEPT data, to give partial structure F (scheme 2). A parallel set of selective INEPT results showed that the N-methyldihydroindole unit, spin system B', and the amide carbon at 168.3 ppm can also be linked together to give partial structure F'. The two partial structures F and F' account for all of the atoms of N-methylepiamauromine, leaving only three degrees of unsaturation to assign.

Irradiation of the methine proton at 5.41 ppm in a selective INEPT experiment (H-2' of substructure F') showed the amide carbon resonance of substructure F (165.3 ppm). This information, as well as the downfield shift of C-2 of the N-methyldihydroindole (82.2 ppm), suggested that C-2 of partial structure F' must be linked to partial structure F through the amide nitrogen of F. The downfield shift of C-2 (79.3 ppm) in the dihydroindole subunit F suggested that it might also be attached to the amide nitrogen of F' in a similar manner, despite the absence of the corresponding correlation in selective INEPT experiments. The downfield shifts of the methine carbons (and protons) alpha to the amide carbonyls also suggested that these carbons are linked to nitrogen. Accordingly, connection of the remaining positions to form a diketopiperazine accounts for the remaining degrees of unsaturation, and leads to assignments of the structure for N-methylepiamauromine.

A nuclear overhauser enhancement/exchange spectroscopy (NOESY) experiment (Table 2) showed correlations between H-2 and H-11, as well as to both methyls of the dimethylpropenyl group. Thus, H-2, H-11 and the dimethylpropenyl group must be on the same face of the ring system. H-2' showed correlations with both methyls of the dimethylpropenyl group and methyl-19', indicating that they are all on the same face of the indole rings. It did not, however, show any correlation with H-11'. H-11' though was correlated to H-11. These results permitted the assignment of the relative stereochemistry as shown for N-methylepiamauromine. The diketopiperazine ring must also be in a boat conformation to make possible a NOESY correlation between H-11 and H-11'. A boat conformation of the diketopiperazine ring has been proposed [Steyn, Tetrahedron 29:107 (1973)] for propyl-2-(1',1'-dimethylallyl)tryptophyl diketopiperazine and for 12S-tetrahydroaustamide, two compounds isolated from *A. ustus*, which are structurally related to N-methylepiamauromine.

TABLE 2

| | Some Pertinent NOESY[a] Correlations for N-methylepiamauromine and Epiamauromine | | | |
|---|---|---|---|---|
| | N-methylepiamauromine | | Epiamauromine | |
| H# | (ppm) | Correlations (#H) | (ppm) | Correlations (H#) |
| 2 | (5.32) | 11, 15, 17, 18 | (5.30) | 11, 15, 17, 18 |
| 10α | (2.45) | 4, 10β, 11 | (2.45) | 4, 10β, 11 |
| 10β | (2.75) | 10α, 11, 15, 17, 18 | (2.75) | 10α, 11 |
| 11 | (4.12) | 2, 10α, 10β, 11', 15, 17, 18 | (4.04) | 2, 10α, 10β, 11' |
| 2' | (5.41) | 10'β, 15', 17', 18', 19' | (5.30) | 15', 17', 18' |
| 10'α | (2.48) | 4', 10'β, 11' | (2.50) | 4', 10'β, 11' |
| 10'β | (2.25) | 2', 10'α, 11', 15', 17', 18' | (2.35) | 10'α, 11' |

TABLE 2-continued

| | Some Pertinent NOESY[a] Correlations for N-methylepiamauromine and Epiamauromine | | | |
|---|---|---|---|---|
| | N-methylepiamauromine | | Epiamauromine | |
| H# | (ppm) | Correlations (#H) | (ppm) | Correlations (H#) |
| 11' | (3.96) | 10'α, 10'β, 11 | (3.90) | 10'α, 10'β, 11 |

[a]600 MHz, in CDCl$_3$.

The $^1$H and $^{13}$C NMR spectra of epiamauromine as well as the one-bond correlations obtained from an HMQC [Klenar and Bax, *J. Magn. Reson.* 71:379 (1987)] experiment (Table 1), were very similar to those of N-methylepiamauromine, except for the absence of the N-methyl signal and the appearance of an exchangeable proton at 4.91 ppm, suggesting that this compound is a demethylated analog of N-methylepiamauromine. This assumption was further supported by the mass spectrum of epiamauromine, which gave a molecular ion at m/z 508. The results of an HMBC [Bax and Summers, *J. Am. Chem. Soc.* 108:2093 (1986) and Bax et al., *J. Am. Chem. Soc.* 108:8056 (1986)] experiment (Table 1) showed correlations analogous to the selective INEPT correlations for N-methylepiamauromine, further supporting proposal of this structure. Epiamauromine has the same gross structure as amauromine [Takase et al., supra (1984) and (1985)]. However, these two compounds differ in stereochemistry. Amauromine is a symmetrical dimer showing only half the signals in the $^1$H and $^{13}$C NMR spectra, while epiamauromine showed all of them. Results of the NOESY experiment (Table 2) indicated that epiamauromine has the same relative stereochemistry as N-methylepiamauromine. Further support for the stereochemistry of epiamauromine and N-methylepiamauromine was provided by comparison of the optical rotations of these two compounds with those of amauromine and other symmetrical compounds [Takase et al., supra] as shown in Table 3. The symmetrical compounds showed considerably higher values for optical rotations compared to epiamauromine and N-methylepiamauromine.

TABLE 3

Optical Rotations of Epiamauromine, N-methylepiamauromine, and the Known Compounds i-vi

| | [δ] | | | [δ] |
|---|---|---|---|---|
| Epiamauromine | −50.0 | iii | | −470.8 |

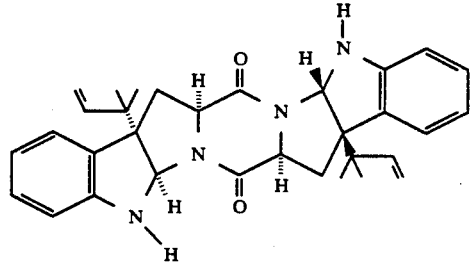
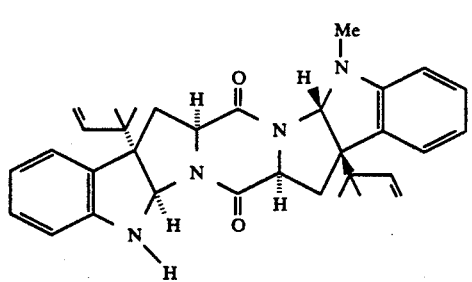

| N-methylepiamauromine | −29.1 | iv | | −433.3 |

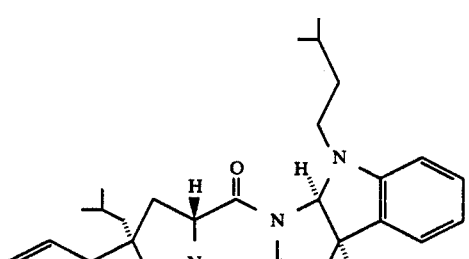
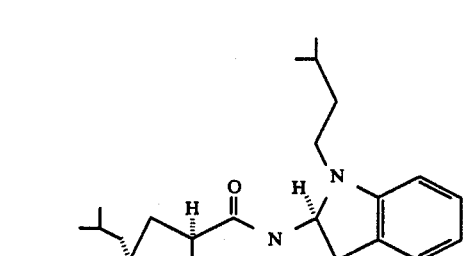

| i | | −583 | v | +202.4 |

TABLE 3-continued
Optical Rotations of Epiamauromine, N-methylepiamauromine, and the Known Compounds i–vi

| [δ] | | [δ] |
|---|---|---| ii  −553    vi  +444

Cycloechinulin, ($C_{20}H_{21}N_3O_3$; HRFAB M+H ion at 352.1670, Δ-1.0 mmu), contains an indole subunit (partial structure H as shown below in Scheme 3), which was substituted at the 6-position with a methoxy group, based on $^1$H decoupling, HMQC and HMBC data (Table 4). Additional evidence for the presence of an indole unit was provided by the UV spectrum which showed absorptions characteristic of an indole with extended conjugation (228, 267, and 300 nm). The presence of an alanyl moiety (I) and subunit J can also be inferred from the NMR data. The methyl protons of subunit J were found to be correlated to C-2 of the indole ring system in the HMBC experiment (Table 4), suggesting linkage of subunit J to the 2-position of the indole. An isolated vinylic proton signal at 7.57 ppm was correlated to both C-2 and C-3 of the indole, indicating linkage of the corresponding double bond to C-3 of the indole as shown in Scheme 3.

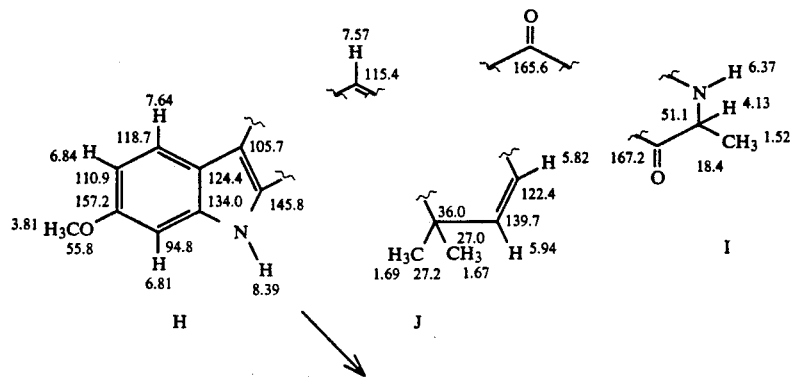

-continued

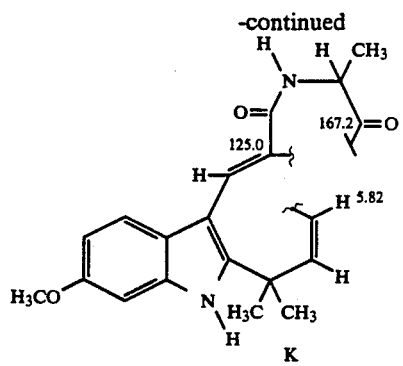

K

TABLE 4
$^1$H and $^{13}$C NMR Data for Cycloechinulin

| Position | $\delta_C{}^a$ (multiplicity$^b$) | $\delta_H{}^c$ (multiplicity, #H: $J_{HH}$) | HMBC$^c$ |
|---|---|---|---|
| 1 | — | 8.39(br s, 1H) | 2, 3, 8, 9 |
| 2 | 145.8 s | — | |
| 3 | 105.7 s | — | |
| 4 | 118.7 d | 7.63(d, 1H; 8.7) | 3, 6, 8 |
| 5 | 110.9 d | 6.84(dd, 1H; 2.2, 8.7) | 7, 9 |
| 6 | 157.2 s | — | |
| 7 | 94.8 d | 6.81(d, 1H; 2.1) | 5, 6, 8, 9 |
| 8 | 134.0 s | — | |
| 9 | 123.4 s | — | |
| 10 | 115.4 d | 7.57(s, 1H) | 2, 3, 9, 12 |
| 11 | 125.0 s | — | |
| 12 | 165.6 s | — | |
| 13 | — | 6.37(br, s 1H) | 11, 14, 15 |
| 14 | 51.1 d | 4.13(dq, 1H; 2.3, 6.9) | 12, 15, 22 |
| 15 | 167.2 s | — | |
| 16 | — | — | |
| 17 | 122.4 d | 5.82(d, 1H; 8.2) | 19, 2$^d$, 11$^d$, 15$^d$, 18$^d$ |
| 18 | 139.7 d | 5.94(d, 1H; 8.2) | 17, 19, 20, 21 |
| 19 | 36.0 s | — | |
| 20 | 27.2 q | 1.68(s, 3H) | 2, 18, 19, 21 |
| 21 | 27.0 q | 1.67(s, 3H) | 2, 18, 19, 20 |
| 22 | 18.4 q | 1.51(d, 3H; 6.9) | 14, 15 |
| 23 | 55.8 q | 3.81(s, 3H) | 6 |

$^a$75 MHz, in CDCl$_3$.
$^b$Multiplicities were obtained from a distortionless enhancement by polarization transfer (DEPT) experiment.
$^c$600 MHz, in CDCl$_3$.
$^d$Correlations shown in selective INEPT experiments, but not in the HMBC data.

The amide proton at 6.37 ppm was found to correlate with an amide carbon at 165.6 ppm, which, in turn, was correlated to the vinylic proton at 7.57 ppm, thus giving rise to partial structure K. Insertion of the remaining nitrogen atom to form a diketopiperazine structure and an 8-membered ring accounts for the molecular formula and the degrees of unsaturation. Confirmation of this structure was provided by irradiation of the vinylic proton at 5.82 ppm in a selective INEPT experiment, which showed carbon signals at 125.0 (C-11) and 167.2 ppm (C-15).

Cycloechinulin is related in structure to the echinulin series of compounds, i.e. echinulin [Quilico, supra], neoechinulins [Marchelli et al., supra (1977)], isoechinulins [Nagasawa et al., Tetrahedron Lett. 1601 (1976)], preechinulin [Stipanovic and Schroeder, Trans. Br. Mycol. Soc. 66:178 (1976)], and cryptoechinuline [Cardillo et al., Tetrahedron Lett. 3163 (1974); Gatti et al., Tetrahedron Lett. 2605 (1978)]. It is uniquely different from these compounds, however, in the condensation of the isoprenyl chain with one of the nitrogens of the diketopiperazine. This linkage has been found in only three other compounds, 10,20-dehydro[12,13-dihydroprolyl]-2-(1',1'-dimethylallyltryptophyl)-diketopiperazine, austamide and 12,13-dihydroaustamide [Steyn, supra and Tetrahedron Lett. 3331 (1971)].

EXAMPLE 2

Insecticidal Activity of N-Methylepiamauromine, Epiamauromine and Cycloechinulin The compounds were evaluated by insect bioassays described previously by Dowd in Entomol. Exp. Appl. 47:69 (1988). Neonate larvae of H. zea were used for all assays. They were obtained from laboratory colonies reared on pinto bean-based diet at 27° C.±1° C., 40±10% relative humidity, and a 14:10 light:dark photoperiod.

The diet used to rear the insects was based on a standard pinto bean diet for many species, which contains the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 2 ml formaldehyde (38%), 1.5 ml of propionic-phosphoric acid solution (42% propionic acid, 4.2% phosphoric acid), and 550 ml water. All dry diet ingredients (except for the pinto beans) were purchased from U.S. Biochemicals Corp. Before use, the beans were soaked in water until saturated (overnight). The agar was added to 250 ml of water and brought to a boil. The other ingredients were blended in a Waring blender until uniformly mixed. The hot agar was added, and blending continued until all ingredients were uniformly mixed.

The pinto bean-based diet thus prepared was added in 5-ml quantities to test tubes. The test tubes were held at 60° C. until chemicals were incorporated to prevent solidification of the diet. A compound of the present invention was added in 125 μl of acetone to the liquid diet to give a final concentration of 370 ppm N-methylepiamauromine or 140 ppm cycloechinulin. Upon addition of the compound, the mixture was removed from the water bath. The chemical was incorporated into the diets by blending vigorously with a vortex mixer for 20 sec. Preliminary observations with colored solutions of both water and acetone indicated uniform incorporation by this method. The diets were dispensed into culture plates and allowed to cool to room temperature. To remove the potentially toxic acetone, the diets were placed in a fume hood for ca. 20 min until slight darkening occurred. The diets were cut into approximately equal sections, and each section was placed into a well of a 24-well immunoassay plate. A single neonate H. zea was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4 and 7 days, and the surviving larvae were weighed after 7 days. Each chemical set was tested on a total of 20 larvae.

Feeding assays using the corn ear worm *Helicoverpa zea* showed that N-methylepiamauromine produced 17.1% reduction in weight gain relative to controls after one week when incorporated into a test diet as described above. Cycloechinulin caused a feeding reduction in adult *C. hemipterus* of 33.3%.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

We claim:

1. A substantially pure diketopiperazine compound selected from the group consisting of:

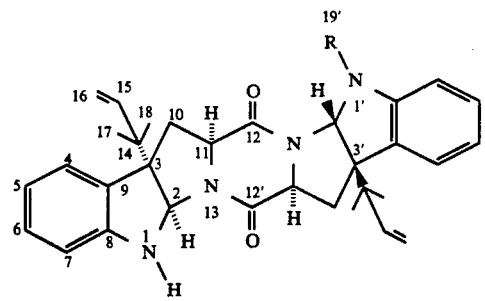

wherein: R is a hydrogen atom or a methyl group, such that the compound formed when R is a hydrogen atom is designated epiamauromine, and the compound formed when R is a methyl group is designated N-methylepiamauromine.

2. A composition for controlling insects comprising: an insecticidally effective amount of an insecticide selected from the group consisting of N-methylepiamauromine and epiamauromine and an inert carrier.

3. The composition of claim 2 wherein the insecticidally effective amount of the insecticide effects of the Lepidoptera species.

4. The composition of claim 2 wherein the insecticidally effective amount of the insecticide effects *Helicoverpa zea*.

5. A method of controlling insects comprising applying an effective amount of an insecticide selected from the group consisting of N-methylepiamauromine and epiamauromine to a locus of insects.

6. The method of claim 2 wherein the insects are Lepidoptera species.

7. The method of claim 5 wherein the inserts are *Helicoverpa zea*.

* * * * *